US005645995A

United States Patent [19]
Kieback

[11] Patent Number: 5,645,995
[45] Date of Patent: Jul. 8, 1997

[54] METHODS FOR DIAGNOSING AN INCREASED RISK FOR BREAST OR OVARIAN CANCER

[75] Inventor: Dirk G. Kieback, Houston, Tex.

[73] Assignee: Baylor College of Medicine, Houston, Tex.

[21] Appl. No.: 629,939

[22] Filed: Apr. 12, 1996

[51] Int. Cl.$^6$ .............................. C12Q 1/68; C12N 15/00
[52] U.S. Cl. .................................. 435/6; 935/77; 935/78
[58] Field of Search ............................ 435/6, 7.1, 91.1, 435/91.2; 530/350; 935/77, 78

[56] References Cited

U.S. PATENT DOCUMENTS

| | | | |
|---|---|---|---|
| 4,742,000 | 5/1988 | Greene | 435/7 |
| 5,283,190 | 2/1994 | Traish et al. | 435/240.27 |
| 5,364,791 | 11/1994 | Vegeto et al. | 435/320.1 |

OTHER PUBLICATIONS

Kieback et al. (1995) Anticancer Res. 15:1766–7.
Garrett et al, "Mendelian Inheritance of a *TaqI* Restriction Fragment Length Polymorphism Due to an Insertion in the Human PR Gene and Its Allelic Imbalance in Breast Cancer", *Cancer Res., Therapy and Control*, pp. 1–8 (1995).
Allgood et al, "Adaptation of a Novel Adenoviral Expression System to Study Function and Covalent Modification of Avian Progesterone Receptor", *76th Endocrine Society Meeting*, Abst. No. 631 (1994).
Tong et al, "A *TaqI* RFLP in the Human Progesterone Receptor Gene (HPR) is Associated with Ovarian Cancer", *ACR Meeting*, 86th Annual Association for Cancer Research, (Preliminary Program), Totonto, Ontario, Canada, Abstract (March 18–22, 1995).
Levy et al, "Chicken Ovalbumin Upstream Promoter—Transcription Factor (COUP–TF–like) Expression in Human Endometrial Cancer Cell Lines", 42nd Annual Society for Gynecologic Investigation, Chicago, Illinois, Abstract (Mar. 15–18, 1995).
Kieback et al, "A Genetic Mutation in the Human Progesterone Receptor Gene (HPR) is Associated with Ovarian Cancer", Society of Gynecological Oncologist, San Francisco, California, Marriott Hotel, 26th Annual Meeting, (Program in Brief), Abstract (Feb. 18–22, 1995).
Kieback et al, "A *TaqI* RFLP in the Human Progesterone Receptor Gene is Associated with Sporadic Epithelial Ovarian Cancer and with Breast Cancer", Society for Gynecologic Invesitgation, 42nd Annual Scientific Meeting (Postgraduate Courses), Chicago, Illinois, Abstract (Mar. 15–18, 1995).
Rowe et al, "The Ovarian Carcinoma–Associated *TaqI* Restriction Fragment Length Polymorphism in Intron G of the Progesterone Receptor Gene is Due to *Alu* Sequence Insertion", *Cancer Research*, 55:2743–2745 (1995).
Zhang et al, "Identification of a Group of Ser–Pro Motif Hormone–Inducible Phosphorylation Sites in the Human Progesterone Receptor", *Mol. Endo.*, 9(8):1029–1040 (1995).

Fuqua et al, "Progesterone Receptor Gene Restriction Fragment Length Polymorphisms in Human Breast Tumors", *J. Nat'l. Cancer Institute*, 83(16):1157–1160 (1991).
Kieback et al, "Die Chemische Heteroduplexspaltung—Ein Verfahren Zur Entdeckung von Mutationen in Östrogen–und Progesteronrezeptorgenen beim Mammakarzinom", *Archives of Gynecology and Obstetrics*, 250(1–4):249–250 (Sep. 11–15, 1990) (and English Translation).
McKenna et al, "A Germline *TaqI* Restriction Fragment Length Polymorphism in the Progesterone Receptor Gene in Ovarian Carcinoma", *British J. of Cancer*, 71:451–455 (1995).
Rodriguez et al, "Dimerization of the Chicken Progesterone Receptor In Vitro Can Occur in the Absence of Hormone and DNA", *Molecular Endocrinology*, 4(11):1782–1790 (1990).
Allan et al, "Ligand–Dependent Conformational Changes in the Progesterone Receptor are Necessary for Events that follow DNA Binding", *Proc. Natl. Acad. Sci., USA*, 89:11750–11754 (1992).
Allan et al, "Hormorne and Antihormone Induce Distinct Conformational Changes Which are Central to Steroid Receptor Activation", *J. Biol. Chem.*, 267(27):19513–19520 (1992).
Sheridan et al, "Synthesis of Human Progesterone Receptors in T47D Cells", *J. Biol. Chem.*, 264(12):7054–7058 (1989).
Tsai et al, "Molecular Mechanisms of Action of Steroid/Thyroid Receptor Superfamily Members", *Ann. Rev. Biochem.*, 63:451–486 (1994).
Zhang et al, "Multiple Signaling Pat).hways Activate the Chicken Progesterone Receptor", *Mol. Endo.*, 8(5):577–584 (1994).
Bai et al, "Phosphorylation of Ser$^{530}$ Facilitates Hormone–Dependent Transcriptional Activation of the Chicken Progesterone Receptor", *Mol. Endo.*, 8(11):1465–1473 (1994).
Agoulnik et al, "Genetic Mutations in the Human Progesterone Receptor Gene Associated with Increased Cancer Risk lead to a Structurally and Functionally Altered Receptor Protein", *Proceedings*, 87th Annual Meeting of the American Association Cancer Research, Washington, D.C., vol. 37, Abstract No. 1514 (Apr. 20–24, 1996).
Kieback et al, "A Complex of Mutations in the Human Progesterone Receptor Gene is Associated with Increased Risk of Non–familial Breast and Ovarian Cancer but not of Uterine Cancer", *Proceedings*, 87th Annual Meeting of the American Association Cancer Research, Washington, D.C., vol. 37, Abstsract No. 1704 (Apr. 20–24, 1996).

*Primary Examiner*—W. Gary Jones
*Assistant Examiner*—Amy Atzel
*Attorney, Agent, or Firm*—Sughrue, Mion, Zinn, Macpeak & Seas

[57] ABSTRACT

The present invention relates to methods for diagnosing an increased risk for breast or ovarian cancer by assaying for genetic markers in the human progesterone receptor gene.

24 Claims, 13 Drawing Sheets

FIGURE 1A

Human Progesterone Receptor cDNA

```
CTGACCAGCG CCGCCCTCCC CCGCCCCCGA CCCAGGAGGT GGAGATCCCT CCGGTCCAGC    60
CACATTCAAC ACCCACTTTC TCCTCCCTCT GCCCCTATAT TCCCGAAACC CCCTCCTCCT   120
TCCCTTTTCC CTCCTCCCTG GAGACGGGGG AGGAGAAAAG GGGAGTCCAG TCGTCATGAC   180
TGAGCTGAAG GCAAAGGGTC CCCGGCTCC CCACGTGGCG GGCGGCCCGC CCTCCCCCGA   240
GGTCGGATCC CCACTGCTGT GTCGCCCAGC CGCAGGTCCG TTCCCGGGGA GCCAGACCTC   300
GGACACCTTG CCTGAAGTTT CGGCCATACC TATCTCCCTG GACGGGCTAC TCTTCCCTCG   360
GCCCTGCCAG GGACAGGACC CCTCCGACGA AAAGACGCAG GACCAGCAGT CGCTGTCGGA   420
CGTGGAGGGC GCATATTCCA GAGCTGAAGC TACAAGGGGT GCTGGAGGCA GCAGTTCTAG   480
TCCCCCAGAA AAGGACAGCG GACTGCTGGA CAGTGTCTTG GACACTCTGT TGGCGCCCTC   540
```

FIGURE 1B

| | | | | | |
|---|---|---|---|---|---|
| AGGTCCCGGG | CAGAGCCAAC | CCAGCCCTCC | CGCCTGCGAG | GTCACCAGCT | CTTGGTGCCT | 600 |
| GTTTGGCCCC | GAACTTCCCG | AAGATCCACC | GGCTGCCCCC | GCCACCCAGC | GGGTGTTGTC | 660 |
| CCCGCTCATG | AGCCGGTCCG | GGTGCAAGGT | TGGAGACAGC | TCCGGGACGG | CAGCTGCCCA | 720 |
| TAAAGTGCTG | CCCCGGGGCC | TGTCACCAGC | CCGGCAGCTG | CTGCTCCCGG | CCTCTGAGAG | 780 |
| CCCTCACTGG | TCCGGGGCCC | CAGTGAAAGCC | GTCTCCGCAG | GCCGCTGCGG | TGGAGGTTGA | 840 |
| GGAGGAGGAT | GGCTCTGAGT | CCGAGGAGTC | TGCGGGTCCG | CTTCTGAAGG | GCAAACCTCG | 900 |
| GGCTCTGGGT | GGCGCGGGCGG | CTGGAGGAGG | AGCCGCGGCT | GTCCCGCCCG | GGGCGGGCAGC | 960 |
| AGGAGGCGTC | GCCCTGGTCC | CCAAGGAAGA | TTCCCGCTTC | TCAGCGCCCA | GGGTCGCCCT | 1020 |
| GGTGGAGCAG | GACGCGCCGA | TGGCGCCCGG | GCGCTCCCCG | CTGGCCACCA | CGGTGATGGA | 1080 |
| TTTCATCCAC | GTGCCTATCC | TGCCTCTCAA | TCACGCCTTA | TTGGCAGCCC | GCACTCGGCA | 1140 |

FIGURE 1C

```
GCTGCTGGAA  GACGAAAGTT  ACGACGGCGG  GGCCGGGGCT  GCCAGCGCCT  TTGCCCCGCC  1200
GCGGAGTTCA  CCCTGTGCCT  CGTCCACCCC  GGTCGCTGTA  GGCGACTTCC  CCGACTGCGC  1260
GTACCCGCCC  GACGCCGAGC  CCAAGGACGA  CGCGTACCCT  CTCTATAGCG  ACTTCCAGCC  1320
GCCCGCTCTA  AAGATAAAGG  AGGAGGAGGA  AGGCGCGGAG  GCCTCCGCGC  GCTCCCCGCG  1380
TTCCTACCTT  GTGGCCGGTG  CCAACCCCGC  AGCCTTCCCG  GATTTCCCGT  TGGGGCCACC  1440
GCCCCCGCTG  CCGCCGCGAG  CGACCCCCATC  CAGACCCGGG  GAAGCGGCGG  TGACGGCCGC  1500
ACCCGCCAGT  GCCTCAGTCT  CGTCTGCGTC  CTCCTCGGGG  TCGACCCTGG  AGTGCATCCT  1560
GTACAAAGCG  GAGGGCGCGC  CGCCCCAGCA  GGGCCCCGTTC  GCGCCGCCGC  CCTGCAAGGC  1620
GCCGGGGCG   AGCGGCTGCC  TGCTCCCGCG  GGACGGCCTG  CCCTCCACCT  CCGCCTCTGC  1680
CGCCGCCCGCC  GGGGCGGCCC  CCGCGCTCTA  CCCTGCACTC  GGCCTCAACG  GGCTCCCGCA  1740
```

FIGURE 1D

```
GCTCGGGCTAC CAGGGCCGCCG TGCTCAAGGA GGGCCCTGCCG CAGGTCTACC CGCCCTATCT   1800
CAACTACCTG AGGCCGGATT CAGAAGCCAG CCAGAGCCCA CAATACAGCT TCGAGTCATT      1860
ACCTCAGAAG ATTTGTTTAA TCTGTGGGGA TGAAGCATCA GGCTGTCATT ATGGTGTCCT      1920
TACCTGTGGG AGCTGTAAGG TCTTCTTTAA GAGGGCAATG GAAGGGCAGC ACAACTACTT      1980
ATGTGCTGGA AGAAATGACT TAAAATCCGC AGAAAAAACT GCCCAGCATG                 2040
TCGCCTTAGA AAGTGCTGTC AGGCTGGCAT GGTCCCTTGGA GGTCGAAAAT TTAAAAAGTT    2100
CAATAAAGTC AGAGTTGTGA GAGCACTGGA TGCTGTTGCT CTCCCACAGC CAGTGGGCGT     2160
TCCAAATGAA AGCCAAGCCC TAAGCCAGAG ATTCACTTTT TCACCAGGTC AAGACATACA     2220
GTTGATTCCA CCACTGATCA ACCTGTTAAT GAGCATTGAA CCAGATGTGA TCTATGCAGG     2280
ACATGACAAC ACAAAACCTG ACACCTCCAG TTCTTTGCTG ACAAGTCTTA ATCAACTAGG     2340
```

FIGURE 1E

```
CGAGAGGCAA CTTCTTTCAG TAGTCAAGTG GTCTAAATCA TTGCCAGGTT TTCGAAACTT    2400
ACATATTGAT GACCAGATAA CTCTCATTCA GTATTCTTGG ATGAGCTTAA TGGTGTTTGG    2460
TCTAGGATGG AGATCCTACA AACACGTCAG TGGGCAGATG CTGTATTTTG CACCTGATCT    2520
AATACTAAAT GAACAGCGGA TGAAAGAATC ATCATTCTAT TCATTATGCC TTACCATGTG    2580
GCAGATCCCA CAGGAGTTTG TCAAGCTTCA AGTTAGCCAA GAAGAGTTCC TCTGTATGAA    2640
AGTATTGTTA CTTCTTAATA CAATTCCTTT GGAAGGGCTA CGAAGTCAAA CCCAGTTTGA    2700
    |INTRON G|←
GGAGATGAGG TCAAGCTACA TTAGAGAGCT CATCAAGGCA ATTGGTTTGA GGCAAAAAGG    2760
AGTTGTGTCG AGCTCACAGC GTTTCTATCA ACTTACAAAA CTTCTTGATA ACTTGCATGA    2820
TCTTGTCAAA CAACTTCATC TGTACTGCTT GAATACATTT ATCCAGTCCC GGGCACTGAG    2880
```

FIGURE 1F

```
TGTTGAATTT CCAGAAATGA TGTCTGAAGT TATTGCTGCA CAATTACCCA AGATATTGGC    2940
AGGGATGGTG AAACCCCTTC TCTTTCATAA AAAGTGAATG TCATCTTTTT CTTTTAAAGA    3000
ATTAAATTTT GTGG                                                     3014

[SEQ ID NO:1]
```

FIGURE 2

EXON 4

```
GTCGAAAATT TAAAAAGTTC AATAAAGTCA GAGTTGTGAG AGCACTGGAT GCTGTTGCTC    60
TCCCACAGCC AGTGGGCGTT CCAAATGAAA GCCAAGCCCT AAGCCAGAGA TTCACTTTTT   120
CACCAGGTCA AGACATACAG TTGATTCCAC CACTGATCAA CCTGTTAATG AGCATTGAAC   180
CAGATGTGAT CTATGCAGGA CATGACAACA CAAAACCTGA CACCTCCAGT TCTTTGCTGA   240
CAAGTCTTAA TCAACTAGGC GAGAGGCAAC TTCTTTCAGT AGTCAAGTGG TCTAAATCAT   300
TGCCAG                                                              306
```

[SEQ ID NO:2]

FIGURE 3

EXON 5

GTTTTCGAAA CTTACATATT GATGACCAGA TAACTCTCAT TCAGTATTCT TGGATGAGCT 60

TAATGGTGTT TGGTCTAGGA TGGAGATCCT ACAAACACGT CAGTGGGCAG ATGCTGTATT 120

TTGCACCTGA TCTAATACTA AATGA 145

[SEQ ID NO:3]

FIGURE 4

INTRON G

```
                                              50
AAAATAAAAAA GAAACTTGAA GGAAATAAAC ACCAGTGCAG AGAACGAAAG
                                              100
AAAACTTCTA ACATCCCTCAG AGAAATAAGA ATGATACGGT ATCCATGACA
                                              149
TGAGAACAGA AAACATTTTT AAAAACAGACA TTTAGCAAGA AAATACGCG
                         ↑
                    Alu Insertion
```

[SEQ ID NO:4]

FIGURE 5

ALU INSERTION

```
TTTTTTTTT  TTTTTTTTT  TTTTGAGAC  GGAGTCTGGC  TCTGTCGCCC  AGGCTGGAGT   60
GCAGTGGCGG  GATCTCGGCT  CACTGCAAGC  TCCGCCTCCC  GGGTTCACGC  CATTCTCCTG  120
CCTCAGCCTC  CCAAGTAGCT  GGGACTACAG  GCGCCCGCCA  CTACGCCCAG  CTAATTTTTT  180
GTATTTTTAG  TAGAGACGGG  GTTTCACCGT  TTTAGCCAGG  ATGGTCTCGA  TCTCCTGACC  240
TCGTGATCCG  CCCGCCTCGG  CCTCCCAAAG  TGCTGGGATT  ACAGGGCGTGA  GCCACCGCGC  300
CCGGCCCAGA  AAACATTTTT                                                 320
```

[SEQ ID NO:5]

METHODS FOR DIAGNOSING AN INCREASED RISK FOR BREAST OR OVARIAN CANCER

FIELD OF THE INVENTION

The present invention relates to methods for diagnosing an increased risk for breast or ovarian cancer by assaying for genetic markers in the human progesterone receptor gene.

BACKGROUND OF THE INVENTION

Breast cancer is the most frequent malignancy in women. A family history of this disease is generally found in approximately 10% of patients afflicted with this disease. In addition, ovarian cancer is the gynecologic tumor with the highest mortality secondary to its insidious onset. A family history of this disease is generally found in approximately 3–5% of patients afflicted with this disease (Koch et al, In. J. Epidemiol., 18:782–785 (1989)). It is these limited groups of patients that will probably benefit most from the recent isolation of the breast cancer gene BRCA-1 (Miki et al, Science, 266:66–71 (1994); and Futreal et al, Science, 266:120–122 (1994)), which offers a likely inroad to a more accurate individual risk assessment in these individuals. The remaining majority of the women at risk have so far been assessed regarding their likelihood to contract these malignancies solely on the basis of anamnestic variables listed in Table 1 (ovarian cancer) and Table 2 (breast cancer) below. Table I represents a meta-analysis of 48 publications, while Table II represents a meta-analysis of 32 publications.

TABLE 1

| Risk Factors for Ovarian Cancer | Cases | Controls | Sensitivity | Specificity | Odds Ratio | 95% Confidence Interval |
|---|---|---|---|---|---|---|
| Years of Education (<12) | 2857 | 10328 | 0.24 | 0.67 | 0.7 | (0.60–0.73) |
| High Social Class | 477 | 1251 | 0.26 | 0.81 | 1.4 | (1.11–1.84) |
| Age of Menarche (<12) | 6493 | 26904 | 0.27 | 0.73 | 1.0 | (0.95–1.07) |
| Age at Natural Menopause (<53) | 1020 | 3085 | 0.22 | 0.79 | 1.1 | (0.89–0.25) |
| Nulliparity | 8554 | 32877 | 0.22 | 0.85 | 1.6 | (1.49–1.68) |
| Nulligravidity | 3334 | 14852 | 0.21 | 0.87 | 1.8 | (1.60–1.95) |
| Age at First Birth (<30) | 3046 | 13120 | 0.16 | 0.90 | 1.6 | (1.40–1.76) |
| No Breast Feeding | 4349 | 12909 | 0.32 | 0.57 | 0.6 | (0.60–0.70) |
| Years of Ovulation (<35) | 2263 | 11489 | 0.36 | 0.74 | 1.5 | (1.40–1.69) |
| No Use of Oral Contraceptives | 6377 | 26345 | 0.74 | 0.42 | 2.1 | (1.97–2.23) |
| Family History of Ovarian Cancer in First Degree Relative | 2385 | 8057 | 0.3 | 0.99 | 3.7 | (2.64–5.23) |
| Family History of Ovarian Cancer in First Degree Relative or Second Degree Relative | 493 | 2465 | 0.7 | 0.98 | 3.3 | (2.13–5.14) |
| Family History of Breast Cancer in First Degree Relative or Second Degree Relative | 752 | 2023 | 0.7 | 0.95 | 1.6 | (1.17–2.34) |
| Family History of Endometrial Cancer in First Degree Relative or Second Degree Relative | 750 | 2023 | 0.5 | 0.96 | 1.2 | (0.79–1.73) |
| Family History of Ovarian, Breast or Endometrial Cancer in First Degree Relative or Second Degree Relative | 5180 | 17672 | 0.5 | 0.98 | 2.4 | (1.99–2.79) |
| Alu Insertion in INTRON G | 65 | 443 | 0.42 | 0.78 | 2.6 | (1.49–4.42) |

TABLE 2

| Risk Factors for Breast Cancer | Cases | Controls | Sensitivity | Specificity | Odds Ratio | 95% Confidence Interval |
|---|---|---|---|---|---|---|
| Atypical Hyperplasia of Breast | 3986 | 4100 | 0.2 | 0.99 | 2.3 | (1.56–3.43) |
| Family History of Breast Cancer in First Degree | 11117 | 11305 | 0.14 | 0.94 | 2.3 | (2.09–2.51) |

TABLE 2-continued

| Risk Factors for Breast Cancer | Cases | Controls | Sensitivity | Specificity | Odds Ratio | 95% Confidence Interval |
|---|---|---|---|---|---|---|
| Relative Family History of Breast Cancer in First Degree Relative or Second Degree Relative | 3408 | 2914 | 0.11 | 0.96 | 2.7 | (2.19–3.31) |
| Family History of Ovarin Cancer in First Degree Relative or Second Degree Relative | 3411 | 2914 | 0.2 | 0.99 | 1.4 | (0.91–2.26) |
| Family History of Endometrial Cancer in First Degree Relative or Second Degree Relative | 3408 | 2914 | 0.4 | 0.96 | 1.2 | (0.93–1.54) |
| No Lactation | 8095 | 20652 | 0.40 | 0.79 | 2.6 | (2.46–2.75) |
| Use of Oral Contraceptives | 4941 | 5547 | 0.56 | 0.44 | 1.0 | (0.92–1.07) |
| Age of Menarche (<12) | 7342 | 7000 | 0.22 | 0.80 | 1.1 | (1.00–1.18) |
| Nulliparity | 17124 | 1963310 | 0.19 | 0.85 | 2.4 | (1.33–1.44) |
| Age at First Birth (<30) | 10062 | 1575465 | 0.28 | 0.83 | 1.9 | (1.80–1.97) |
| Alcohol Intake (<20 g/day) | 519 | 1182 | 0.17 | 0.86 | 1.2 | (0.92–1.62) |
| Hair Dye Use | 391 | 780 | 0.25 | 0.78 | 1.2 | (0.88–1.56) |
| Alu Insertion in INTRON G | 164 | 443 | 0.28 | 0.78 | 1.37 | (0.91–2.06) |

Estrogen and progesterone receptor expression in the tumor itself have been established as prognostic factors (McGuire, Rec. Prog. Horm. Res., 36:135–149 (1980); Kieback et al, Cancer Research, 53:5188–5192 (1993); and Kieback et al, Anticancer Research, 13:2489–2496 (1993)). Also, somatic mutations in the progesterone receptor gene have been described in this context (Fuqua et al, J. Natl. Cancer Inst., 83:1157–1160 (1991); and Kieback et al, Berichte Gynäkologie und Geburtshilfe, 127:1020 (1990)). However, there has been a lack of information on the existence and possible clinical and biological significance of genomic alterations in steroid receptor genes.

Recently, a genomic factor has been described that would permit further stratification. That is, a genomic Restriction Fragment Length Polymorphism (RFLP) in the human progesterone receptor gene located on the long arm of chromosome 11 (Law et al, Proc. Natl. Acad. Sci., USA, 84:2877–2881 (1987); and Rousseau-Merk et al, Hum. Genet., 77:280–282 (1987)) has been discovered (Genome Data Base #G00-390-114). Its clinical association with ovarian and breast cancer have recently been demonstrated to be associated with an Alu insertion within INTRON G of the human progesterone receptor gene (McKenna et al, Brit. J. Cancer, 71:451–455 (1995); and Rowe et al, Cancer Res., 55:2743–2745 (1995)).

The Alu insertion is in an intron which does not cause a change in the receptor protein. However, changes in the protein are biologically important for the development of disease, as well as for tumor cell growth. Thus, in the present invention, the exons of the progesterone receptor gene were screened for mutations. Point mutations in EXON 4 and EXON 5 were discovered in the present invention to be associated with the Alu insertion in INTRON G, and thereby with an increased risk for breast cancer and ovarian cancer. In all of the cases evaluated, these three mutations were found to simultaneously occur.

SUMMARY OF THE INVENTION

An object of the present invention is to provide a method for diagnosing an increased risk for breast cancer.

Another object of the present invention is provide a method for diagnosing an increased risk for ovarian cancer.

These and other objects of the present invention, which will be apparent from the detailed description of the invention provided hereinafter, have been met, in one embodiment, by a method for diagnosing an increased risk for breast or ovarian cancer comprising the steps of:

(A) obtaining, from a test subject, test nucleic acid comprising codon 660 within EXON 4 of the human progesterone receptor gene; and (B) assaying for the presence of a G to T point mutation in the first nucleotide of codon 660 within EXON 4 of the human progesterone receptor gene, wherein the presence of said point mutation in said test nucleic acid indicates an increased risk for breast or ovarian cancer.

BRIEF DESCRIPTION OF THE DRAWINGS

FIGS. 1A–1F show the cDNA sequence encoding the human progesterone receptor gene (SEQ ID NO:1). In FIGS. 1A–1F, EXON 4 is underlined, EXON 5 is in bold, and the location of INTRON G is noted. In FIGS. 1A–1F, the site for mutational analysis within EXON 4, i.e., nucleotide 2153, is underlined and italicized, the site for mutational analysis within EXON 5 is also underlined and italicized, i.e., nucleotide 2485, and the site for INTRON G, i.e., between nucleotides 2644 and 2645, is noted.

FIG. 2 shows the DNA sequence encoding EXON 4 of the human progesterone receptor gene (SEQ ID NO:2). In FIG. 2, the site for mutational analysis within EXON 4, i.e., within codon 660 of the human progesterone receptor gene, is underlined and italicized.

FIG. 3 shows the DNA sequence encoding EXON 5 of the human progesterone receptor gene (SEQ ID NO:3). In FIG. 3, the site for mutational analysis within EXON 5, i.e., within codon 770 of the human progesterone receptor gene, is underlined and italicized.

FIG. 4 shows the DNA sequence encoding INTRON G of the human progesterone receptor gene (SEQ ID NO:4). In FIG. 4, the site for mutational analysis within INTRON G of the human progesterone receptor gene, which is located within codon 897, i.e., the Alu insertion, is noted.

FIG. 5 shows the DNA sequence encoding the Alu insertion (SEQ ID NO:5).

DETAILED DESCRIPTION OF THE INVENTION

Figure 6:
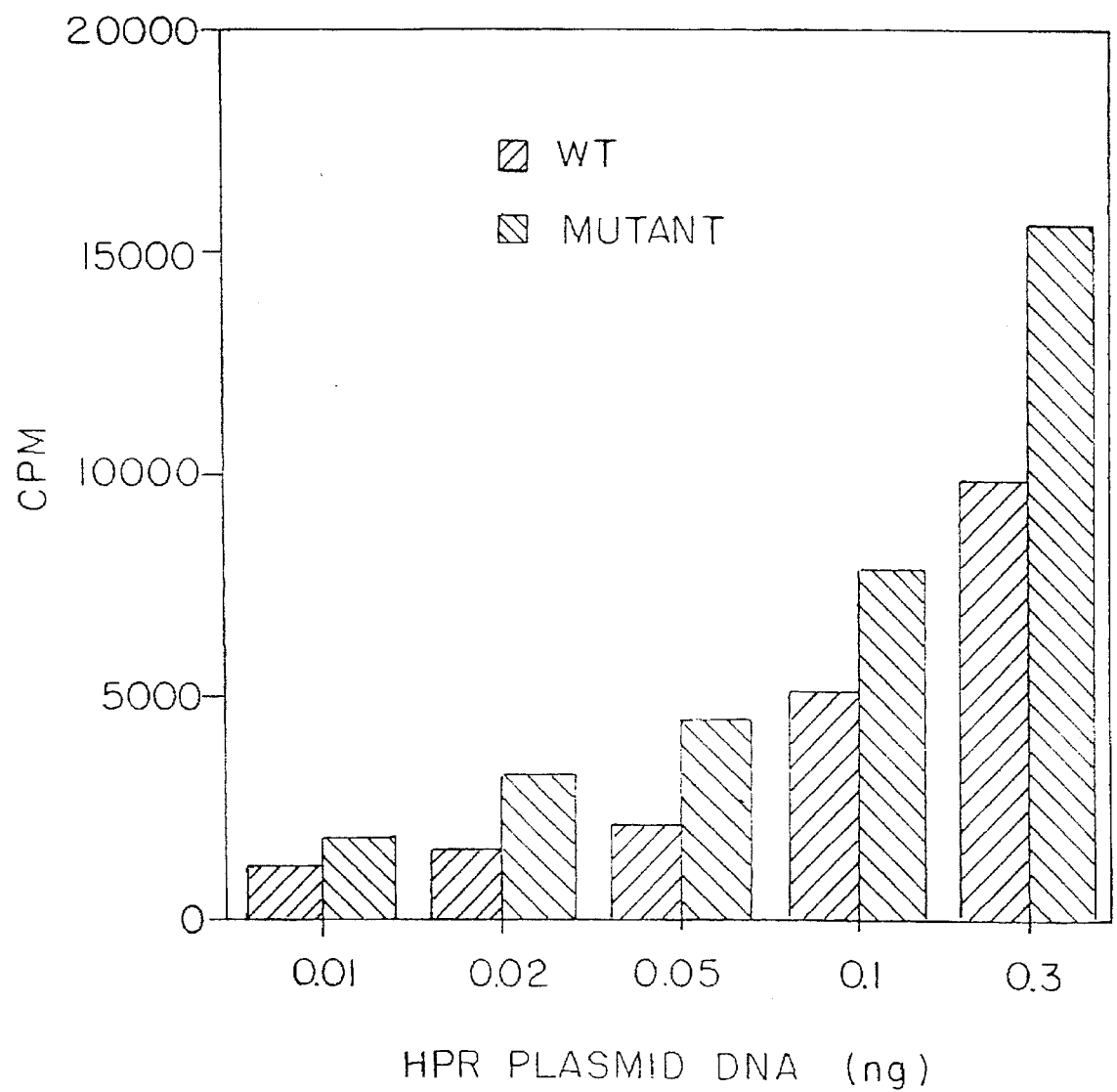
FIG. 6 shows the results of transcriptional activity assays performed using COS cells expressing wild-type (WT) or mutant human progesterone receptor (PR) in a concurrent CAT assay.

As discussed above, in one embodiment, the above described objects of the present invention have been met by a method for diagnosing an increased risk for breast or ovarian cancer comprising the steps of:

(A) obtaining, from a test subject, test nucleic acid comprising codon 660 within EXON 4 of the human progesterone receptor gene; and (B) assaying for the presence of a G to T point mutation in the first nucleotide of codon 660 within EXON 4 of the human progesterone receptor gene, wherein the presence of said point mutation in said test nucleic acid indicates an increased risk for breast or ovarian cancer.

In the above assay, the detection of the point mutation gives an odds ratio for ovarian cancer of 3.1 (sensitivity 46%, specificity 78%), and an odds ratio for breast cancer of 2.0 (sensitivity 36%, specificity 78%).

The particular means for assaying for the presence of a G to T point mutation in the first nucleotide of codon 660 within EXON 4 of the human progesterone receptor gene in step (B) is not critical to the present invention. For example, said assaying in step (B) can be carried out by subjecting said test nucleic acid to BsrI restriction enzyme digestion, and assaying for the destruction of an BsrI restriction site within EXON 4 of the human progesterone receptor gene, as described by Sambrook et al, Molecular Cloning A Laboratory Manual, 2nd Edition, Cold Spring Harbor Press (1989) at Vol. 1, 15.16–5.32. In this assay, the destruction of said restriction site indicates the presence of said point mutation.

Alternatively, said assaying in step (B) can be carried out by sequencing said test nucleic acid using any conventional sequencing method, as described by Sambrook et al, supra at Vol. 2, 13.2–13.102.

In a preferred embodiment, said method additionally comprises the steps of:

(C) obtaining, from said test subject, test nucleic acid which comprises codon 770 within EXON 5 of the human progesterone receptor gene, and (D) assaying for the presence of a C to T point mutation in the third nucleotide of codon 770 within EXON 5 of the human progesterone receptor gene, wherein the presence of said point mutation in said test nucleic acid indicates an increased risk for breast or ovarian cancer.

In the above assay, the detection of the point mutation also gives an odds ratio for ovarian cancer of 3.1 (sensitivity 46%, specificity 78%), and an odds ratio for breast cancer of 2.0 (sensitivity 36%, specificity 78%).

The particular means for assaying for the presence of a C to T point mutation in the third nucleotide of codon 770 within EXON 5 of the human progesterone receptor gene in step (D) is not critical to the present invention. For example, said assaying in step (D) can be carried out by subjecting said test nucleic acid to NlaIII restriction enzyme digestion, and assaying for the creation of a NlaIII restriction site within EXON 5 of the human progesterone receptor gene, as described by Sambrook et al, supra at Vol. 1, 5:16–5.32. In this assay, the creation of said restriction site indicates the presence of said point mutation.

Alternatively, assaying in step (D) can be carried out by sequencing said test nucleic acid, using any conventional technique, as described by Sambrook et al, supra at Vol. 2, 13:2–13.102.

Assaying in steps (B) and (D) can also be carried out by single-strand conformation polymorphism analysis (hereinafter "SSCP"), as described by Orita et al, *Proc. Natl. Acad. Sci., USA*, 86:2766–2770 (1989); Gaidamo et al, Proc. Natl. Acad. Sci., USA, 88:5413–5417 (1991); and Orita et al, *Genomics*, 5:874–879 (1989).

SSCP is a simple and efficient technique for the detection of single base substitutions. This method is based on the assumption that changes in the nucleotide sequence affect single-strand conformation, and thus results in altered electrophoretic mobility.

In addition, assaying in steps (B) and (D) can be carried out by heteroduplex mapping, as described by Negamine et al, *Am. J. Hum. Genet.*, 45:337–339 (1989); and Keen et al, *Trends in Genetics*, 7:5 (1991)).

In a most preferred embodiment, said method additionally comprises the steps of:

(E) obtaining, from said test subject, test nucleic acid which comprises codon 897 within INTRON G of the human progesterone receptor gene, and (F) assaying for the presence of an Alu insertion within codon 897 within INTRON G of the human progesterone receptor gene, wherein the presence of said Alu insertion in said test nucleic acid indicates an increased risk for breast or ovarian cancer.

In the above assay, the detection of the point mutation also gives an odds ratio for ovarian cancer of 3.1.(sensitivity 46%, specificity 78%), and an odds ratio for breast cancer of 2.0 (sensitivity 36%, specificity 78%).

The odds ratios are the same for the assays involving EXON 4, EXON 5 and INTRON G, since as discussed above, in all of the cases evaluated, these three mutations were found to simultaneously occur.

The particular means for assaying for the presence of an Alu insertion within INTRON G of the human progesterone receptor gene in step (F) is not critical to the present invention. For example, said assaying in step (F) can be carried out by subjecting said test nucleic acid to TaqI restriction enzyme digestion, and assaying for the production of a 1.9 kb DNA fragment, as described by McKenna et al, *Brit. J. Cancer,* 71:451–455 (1995). In this assay, the production of said 1.9 kb DNA fragment indicates the presence of said Alu insertion.

Alternatively, assaying in step (F) can be carried out by polymerase chain reaction using forward and reverse primers that border or are within INTRON G, as described by Rowe et al, *Cancer Res.*, 55:2743–2745 (1995).

When carrying out a polymerase chain reaction to assay for an Alu insertion in INTRON G, the particular primers employed are not critical to the present invention. Examples of such primers are those that boarder INTRON G, e.g., wherein the forward primer is:

5'-TTGATAACTTGCATGATGTAAGTA-3' (SEQ ID NO: 6),
and the reverse primer is:
5'-TGAAGTTGTTTGACAAGCTGTTGG-3' (SEQ ID NO: 7), or those that are within INTRON G, e.g., wherein the forward primer is:
5'-GCCTCTAAAATGAAAGGCAGAAAGC-3' (SEQ ID NO: 8)
and the reverse primer is:
5'-CAAAAGTATTTTGTTGCTAAATGTCTG-3' (SEQ ID NO: 9).

SEQ ID NO:6 corresponds to nucleotides −17 to +7 of the boundary of EXON 7 and INTRON G; SEQ ID NO:7 corresponds to nucleotides +17 to −7 of the boundary of EXON 8 and INTRON G; SEQ ID NO:8 corresponds to nucleotides 811 to 835 of INTRON G; and SEQ ID NO:9 corresponds to nucleotides 1280 to 1306 of INTRON G.

As another alternative, said assaying in step (F) can be carried out by sequencing said test nucleic acid, using any conventional technique, as described by Sambrook et al, supra at Vol. 2, 13.2–13.102.

In addition, assaying in step (F) can be carried out by heteroduplex mapping, as described by Negamine et al, *Am. J. Hum. Genet.*, 45:337–339 (1989); and Keen et al, *Trends in Genetics*, 7:5 (1991)).

Said assaying in step (F) can also be carried out by Southern blotting using a cDNA of the human progesterone receptor gene as a probe, as described by Sambrook et al, supra at Vol. 2, 9.31–9.62.

The Alu insertion can also be detected with florescent in situ hybridization by analogy to the detection of specific sites on chromosomes. Thus, the Alu insertion can be detected using a random primer. For example, a random primed in situ labelling technique or multiple sequential oligonucleotide-primed in situ DNA synthesis reaction can be used to determine the presence of the Alu insertion (Pellestor et al, *Hum. Genet.*, 95:12–17 (1995); and Speel et al, *Hum. Genet.*, 95:29–33 (1995)). The sequence of the primer may be, e.g.: 5'-AAAGTGCTGGGATTACAGG-3' (SEQ ID NO:10).

In the method of the present invention, the source of the test nucleic acid is not critical. For example, the test nucleic acid can be obtained from cells within a body fluid of said subject or from cells constituting a body tissue of said subject.

The particular body fluid from which the cells is obtained is also not critical to the present invention. For example, the body fluid may be selected from the group consisting of blood, ascites, pleural fluid and spinal fluid.

Furthermore, the particular body tissue from which the cells is obtained is also not critical to the present invention. For example, the body tissue may be selected from the group consisting of skin, endometrial, uterine and cervical tissue. Both normal and tumor tissues can be used.

When assaying for the mutation in EXON 4 or EXON 5, the test nucleic acid can be, e.g., genomic DNA, cDNA obtained from mRNA or mRNA, depending on the assay means employed, e.g., mRNA can be sequenced to identify the mutations in EXON 4 and EXON 5. However, when assaying for the mutation in EXON 4 or EXON 5, the test nucleic acid is preferably genomic DNA.

When assaying for the mutation in INTRON G, the test nucleic acid is genomic DNA.

Genomic DNA can be obtained, e.g., as described by Miller et al, *Nucl. Acids Res.*, 16:1215 (1988), and cDNA can be obtained by standard techniques in the art using isolated mRNA as template.

Furthermore, the test nucleic acid obtained in steps (A), (C) and (E) may be the same or different.

As an alternative to the above-described DNA-based assays, the mutation in EXON 4 can be assayed for by using an antibody which distinguishes between human progesterone receptor protein which contains a valine to leucine substitution at amino acid 660, and wild-type human progesterone receptor protein. The antibody can be polyclonal or monoclonal, and can be prepared as described by Sambrook et al, supra at Vol. 3, 18.16–18.18, using purified antigen (either wild-type or mutant human progesterone receptor protein) which is obtained as described by Zang et al, *Mol. Endocrinol.*, 8:1029–1040 (1995)). The human progesterone receptor protein (antigen) can be obtained by, e.g., immunoprecipitation with a commercially available progesterone receptor antibody, such as PgR AB-2 (NeoMarkers; Freemont, Calif.), as described by Sambrook et al, supra at Vol. 3, 18.44–18.46.

The antibody-based assay can be, e.g., an immunohistochemical assay, and carried out as described by Sambrook et al, supra at Vol. 2, 9.31–9.62; and Press et al, *Lab. Invest.*, 50:480–486 (1984), or a Western blot assay, and carried out as described by Sambrook et al, supra at Vol. 3, 18.60–18.75, only substituting the progesterone antibody with an antibody which distinguishes between human progesterone receptor protein which contains a valine to leucine point mutation at amino acid 660, and wild-type human progesterone receptor protein.

In another alternative to the above-described DNA-based assays, the mutation in EXON 4 can be assayed for by comparing receptor stabilities (Sheridan et al, *J. Biol. Chem.*, 264:7054–7058 (1989)), dimerization (Rodriguez et al, *Mol. Endo.*, 4:1782–1790 (1990)), or binding to the progesterone receptor response element (Allan et al, *Proc. Natl. Acad. Sci.*, USA, 89:11750–11754 (1992); and Allan et al, *J. Biol. Chem.*, 267:19513–19520 (1992)) or to activators (Tsai et al, *Ann. Rev. Biochem.*, 63:451–486 (1994)).

The following examples are provided for illustrative purposes only and are in no way intended to limit the scope of the present invention.

EXAMPLE 1

SSCP Assay for Mutations in EXON 4 and EXON 5

A. EXON 4 Assay

Genomic DNA was obtained from blood samples. More specifically, the blood samples were centrifuged at 3000 rpm for 15 min, and then the "buffy coat" of white blood cells was removed. The resulting red blood cells were lysed for 10 min in 10 ml of lysis buffer comprising 155 mM $NH_4Cl$, 10 mM $NH_4HCO_3$ and 0.1 mM EDTA (pH 7.40). This step was repeated after centrifugation at 1200 rpm. Thereafter, genomic DNA extraction was carried out on the lysed red blood cells as describe by Miller et al. *Nucl. Acids Res.*, 16:1215 (1988).

Next, the following forward and reverse primers, respectively, were synthesized, and used to amplify EXON 4 of the human progesterone receptor gene using the genomic DNA as template:

5'-GGAATTCGTCGAAAATTTAAAAAGTTCA-3' SEQ ID NO: 11)
5'-GGAATTCCTGGCAATGATTTAGACCACT-3' (SEQ ID NO: 12).

SEQ ID NO:11 corresponds to nucleotides 2082 to 2102 of the human progesterone receptor cDNA; and SEQ ID NO:12 corresponds to nucleotides 2387 to 2367 of the human progesterone receptor cDNA.

The DNA sequence in italics is an arbitrarily added synthetic restriction site that is non-specific, and may be changed or omitted.

More specifically, a 10 μl PCR reaction mixture was prepared containing 10 pmol of each EXON 4 primer, 2.5 μM of each dNTP, 1.0 μCi of ($\alpha$-$^{32}$P)dCTP (3000 Ci/mmol; 1.0 Ci=37 GBq, Amersham, Mass.), 100 ng of genomic DNA, 0.02 units of thermostable Taq polymerase (Amplitaq, Perkin-Elmer/Cetus), 5.0 mM KCl, 1.0 mMTris-HCl (pH 8.3) and 0.15 mM $MgCl_2$. Then, the PCR was run for 30 cycles in a thermocycler (MJ Research, PTC-100) at 92° C. for 30 sec, at 60° C. for 45 sec, and at 72° C. for 1 min, with an initial denaturing step at 94° C. for 1 min.

Thereafter, 1.0 μl of the resulting reaction mixture, to which 5.0 μl of stop solution comprising 95% (v/v) formamide, 20 mM EDTA, 20 mM NaOH, 0.05% (w/v) bromophenol blue, and 0.05% (w/v) xylene cyanol FF, was added, was subjected to electrophoresis on a 42 cm long non-denaturing 7.0% (w/v) polyacrylamide gel at constant wattage (7 watts) in 0.6×TBE buffer for 14 hr. TBE buffer comprises 90 mM Tris (pH 8.0), 90mM boric acid and 2.0 mM EDTA.

The resulting gel was then dried, and exposed to X-ray film overnight.

In the mutant homozygous state, a band which runs slightly more slowly than the normal band was seen. In the heterozygous state, a combination of the normal and mutant bands was seen.

B. EXON 5 Assay

The following forward and reverse primers respectively, were used to amplify EXON 5 of the human progesterone receptor gene using the genomic DNA obtained as described above as template:

5'-GGAATTCGTTTTCGAAACTTACATATTG-3' (SEQ ID NO: 13)
5'-GGAATTCTCATTTAGTATTAGATCAGGT-3' (SEQ ID NO: 14)

SEQ ID NO:13 corresponds to nucleotides 2388 to 2408 of the human progesterone receptor cDNA; and SEQ ID NO:14 corresponds to nucleotides 2532 to 2512 of the human progesterone receptor cDNA.

Again, the DNA sequence in italics is an arbitrarily added synthetic restriction site that is non-specific, and may be changed or omitted.

More specifically, a 10 μl PCR reaction mixture was prepared containing 10 pmol of each EXON 5 primer, 2.5 μM of each dNTP, 1.0 μCi of ($\alpha$-$^{32}$P)dCTP (3000 Ci/mmol; 1.0 Ci=37 GBq, Amersham, Mass.), 100 ng of genomic DNA, 0.02 units of thermostable Taq polymerase (Amplitaq, Perkin-Elmer/Cetus), 5.0 mM KCl, 1.0 mM Tris-HCl (pH 8.3) and 0.15 mM $MgCl_2$. Then, the PCR was run for 30 cycles in a thermocycler (MJ Research, PTC-100) at 92° C. for 30 sec, at 60° C. for 45 sec, and at 72° C. for 1 min, with an initial denaturing step at 94° C. for 1 min.

Thereafter, 1.0 μl of the resulting reaction mixture, to which 5.0 μl of stop solution, was added, was subjected to electrophoresis on a 42 cm long non-denaturing 7.0% (w/v) polyacrylamide gel at constant wattage (5 watts) in 0.6×TBE buffer for 14 hr.

The resulting gel was then dried, and exposed to X-ray film overnight.

In the mutant homozygous state, a band which runs slightly more slowly than the normal band was seen. In the heterozygous state, a combination of the normal and mutant bands was seen.

EXAMPLE 2

Restriction Assay for Mutations in EXON 4 and EXON 5

EXON 4 Assay

The DNA sequence of codons 659–660 (CCAGTG) of the human progesterone receptor gene contains a recognition site (CCAGT) for the restriction endonuclease BsrI. The change of the nucleotide sequence in codon 660 (GTG to TTG; Val to Leu) within EXON 4 will not allow restriction cleavage with BsrI at this site.

Accordingly, a 320 bp DNA fragment encompassing codon 660 was amplified using the primer pair for EXON 4 described in Example 1 above. The amplified DNA fragment contains two other recognition sites for BsrI, i.e., at codons 652 and 697.

More specifically, a 10 μl PCR reaction mixture was prepared containing 50 ng of genomic DNA, 50 nM of each EXON 4 primer, 20 μM of each dNTP, 5.0 mM KCl, 10 mM Tris-HCl (pH 8.3), 0.15 mM $MgCl_2$, and 0.2 units of Taq DNA polymerase. Then, the PCR was run for 30 cycles in a thermocycler (MJ Research PTC-100) at 92° C. for 30 sec, at 60° C. for 45 sec, and at 72° C. for 1 min, with a initial denaturing step at 94° C. for 1 min, followed by BsrI digestion for 2 h at 65° C., as described by the manufacture (New England Biolab), and subjected to 1.5% (w/v) polyacrylamide electrophoresis or 10% (w/v) non-denaturing acrylamide gel in 1×TBE buffer for 4 hr, and then stained with ethidium bromide.

BsrI cleavage of the PCR-amplified wild-type DNA fragment resulted in the following four DNA fragments from 5' to 3': 56 bp, 20 bp, 157 bp and 87 bp. On the other hand, BsrI cleavage of the mutant DNA fragment, i.e., having the mutation at codon 660, resulted in the following three DNA fragments: 55 bp, 177 bp and 86 bp. In the heterozygous state, the large 177 bp fragment was seen in addition to the 157 bp fragment. In the homozygous state, only the large 177 bp fragment was seen.

B. EXON 5 Assay

A new recognition site (CATG) for the restriction endonuclease NlaIII is created through the mutation in codon 770 (CAT to CAC, no amino acid change). The change of the nucleotide sequence in codon 770 within EXON 5 allows restriction cleavage with NlaIII at this site.

Accordingly, a 159 bp DNA fragment encompassing codon 770 using amplified using the primer pair for EXON 5 described in Example 1 above.

More specifically, a 10 μl PCR reaction mixture was prepared containing 50 ng of genomic DNA, 50 nM of each EXON 5 primer, 20 μM of each dNTP, 5.0 mM KCl, 10 mM Tris-HCl (pH 8.3), 0.15 mM $MgCl_2$, and 0.2 units of Taq DNA polymerase. Then, the PCR was run for 30 cycles in a thermocycler (MJ Research PTC-100) at 92° C. for 30 sec, at 54° C. for 45 sec, and at 72° C. for 1 min, with a initial denaturing step at 94° C. for 1 min, followed by NlaIII digestion for 2 hr at 37° C., as described by the manufacturer (New England Biolab), and subjected to 1.5% (w/v) polyacrylamide electrophoresis or 10% (w/v) non-denaturing acrylamide gel in 1×TBE buffer for 4 hr, and then stained with ethidium bromide.

NlaIII cleavage of the PCR-amplified wild-type DNA fragment resulted in only one DNA fragment of 159 bp. On the other hand, NlaIII cleavage of the mutant DNA fragment, i.e., having the mutation at codon 770, resulted in the following two DNA fragments from 5' to 3': 106 bp and 53 bp. In the heterozygous state, the uncut fragment of 159 bp was seen in addition to 106 bp and 53 bp bands. In the homozygous state, the 159 bp fragment was not seen.

EXAMPLE 3

DNA Sequencing Assay for Mutations in EXON 4 and EXON 5

The PCR products containing EXON 4 and EXON 5 obtained in Example 1 above, were purified through centricon-100 (Amicon, Inc., MA) . Thereafter, the same primers used for amplification of EXON 4 and EXON 5 were used for cycle-sequencing. Cycle-sequencing was performed using the dsDNA Cycle Sequencing System kit (Gibco BRL, NY).

The presence of a G to C point mutation in the third nucleotide of codon 770 within EXON 5 of the human progesterone receptor gene was found, which is a silent third base change. The G to T point mutation in codon 660 within EXON 4 lead to an amino acid change of valine to leucine, thereby giving rise to a mutant human progesterone receptor protein.

The sequencing results did not distinguish homozygosity from heterozygosity because the predominant sequencing pattern depends on the fragment that is preferentially amplified during the PCR reaction, which cannot be foreseen in the individual case. Co-existing patterns in the normal and the mutated state may be present.

EXAMPLE 5

Assay for Alu Insertion in INTRON G

Southern blotting was carried out using, as a probe, a 1846 bp cDNA fragment encompassing from 1084 bp of the 3'-coding region to 767 bp of the 5'-untranslated region of the human progesterone receptor gene.

More specifically, 20 μg of genomic DNA was digested with TaqI overnight at 65° C., and subjected to electrophoresis on a 0.8% (w/v) agarose gel for 22 hr at 35 volts in 1×TAE buffer comprising 40 mM Tris base, 40 mM glacial acetic acid and 1.0 mM EDTA. The resulting gel was subjected to Southern blotting onto a nylon membrane. Hybridization was carried out overnight using 50 ng of radioactive probe, labelled with 50 μCi of $^{32}P$, for each 20 cm×20 cm membrane in a total volume of 20 ml hybridization buffer comprising 8.0% (w/v) dextranesulfate, 75 mM NaCl, 7.5 mM Na citrate-dihydrate, 5×Denhardt's solution, 0.5% (w/v) SDS and 500 μg salmon sperm DNA. A final wash was carried out using 1×SSC containing 0.1% (w/v) SDS at 65° C. for 10 min. The membrane was air dried and exposed to Kodak X-ray film or analyzed with a Beta-scope.

There is an additional 1.9 kb fragment (band) in some individuals when compared to the normal pattern, indicating the presence of a polymorphism. This fragment (band) appears in addition to the normal 2.7 kb and 1.4 kb fragments (bands) in the heterozygous state. In the homozygous state, the normal 2.7 kb fragment (band) disappears, and only the 1.9 kb fragment (band) appears. In this state, the 1.4 kb fragment (band) remains unchanged.

EXAMPLE 6

Protein Assays for Mutation in EXON 4

A. Transcriptional Activity Assay

Transcriptional activities of wild-type and mutant progesterone receptor proteins were compared in concurrent CAT assays.

More specifically, COS cells, which do not possess endogenous progesterone receptors, were plated into 6-well cluster plates at a density of $9.0 \times 10^4$ cells per well approximately 24 hrs prior to infection. The cells were then infected, as described by Sambrook et al, supra at Vol. 2, 16.33–16.37, with 0.01–0.3 ng of cDNA encoding either Mutant or wild-type progesterone receptor. The wild-type or mutant human progesterone receptor cDNA used had been cloned into the BamHI site of pcDNAI/Amp vector (Intvitrogen). Next, the infected cells were incubated in DME containing 5.0% (v/v) fetal calf serum and 10 nM R5020 (a modified progesterone) (DuPont NEN), for 24 hrs before harvesting. Then, the cells were harvested and assayed for CAT activity, as described by Zhang et al, Mol. Endo., 8:577–584 (1994)). The results are shown in FIG. 6.

As shown in FIG. 6, hormone-induced transcriptional activity of the mutant progesterone receptor DNA was about 30% higher than that for the wild-type receptor DNA. Each data point was tested in duplicate, and the results have been found to be reproducible with different preparations of both the mutant and wild-type receptor DNA.

B. Hormone-Binding Assay

To determine whether the increase in transcriptional activity found above was due to changes in hormone-binding affinity, hormone binding affinity was measured in a Whole Cell Assay, as described by Bai et al, Mol. Endo., 8(11): 1465–1473 (1994), using DNA encoding both the mutant and wild-type progesterone receptor proteins.

More specifically, COS cells were infected with 250 ng of either mutant or wild-type receptor DNA, as described above, and the infected cells were incubated overnight in DME containing 5.0% (v/v) fetal calf serum and 50–6400 pM of [$^3$H]R5020 (DuPont NEN, NET-555) before harvesting. Next, the harvested cells were subjected to ethanol extraction, and bound hormone was measured by CPM counting of the extracts. The results are shown in FIG. 7A.

Figure 7A:
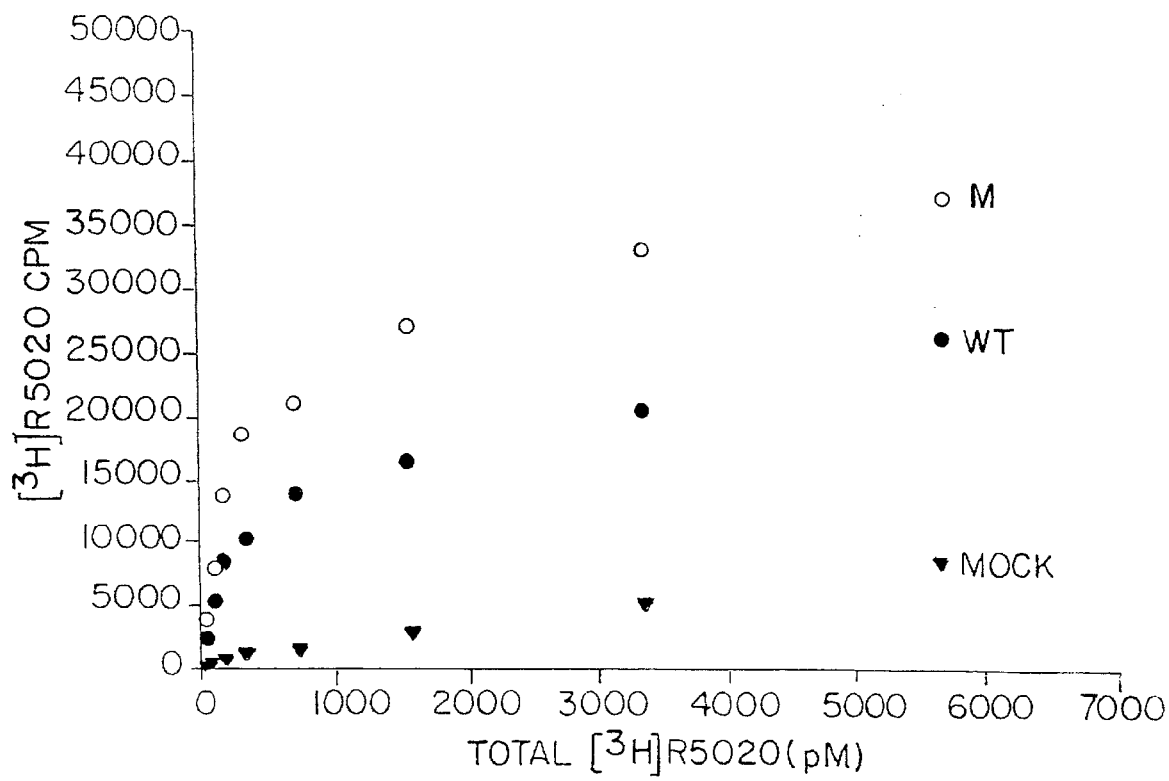
FIG. 7A shows the results of hormone-binding affinity assays performed using COS cells expressing wild-type or mutant human progesterone receptor proteins.
Figure 7B:
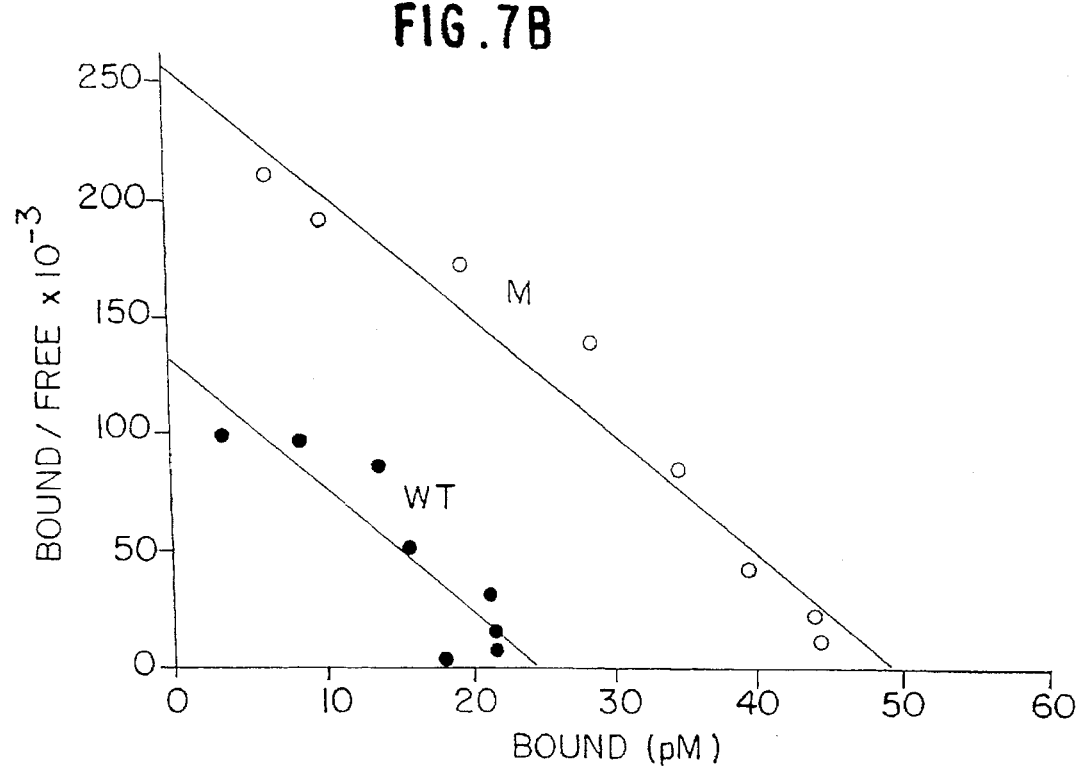
FIG. 7B shows Scatchard analyses of these data.

As shown in FIG. 7A, the hormone-binding assay detected saturable and specific progesterone binding for both mutant and wild-type receptors. Scatchard analyses of these data, which is shown in FIG. 7B, yielded values of 0.25 nM for the dissociation constant for both the mutant and the wild-type receptor.

C. Protein Levels

To further investigate the cause of the elevated transcriptional activity of the mutant receptor DNA, the levels of protein were measured by the Whole Cell Assay (Bai et al, supra) and a Western blot assay.

More specifically, COS cells were infected with 0.25–15 ng of either mutant or wild-type receptor DNA as described above. The cells were then incubated for 48 hrs in DMEM containing 5.0% (v/v) fetal calf serum which had been stripped which charcoal. 2 hrs prior to ethanol extraction, 1.0 nM R5020 was added to the media. The Whole Cell Assay was performed as described by Bai et al, Mol. Endo., 8(11):1465–1473 (1994). The results are shown in FIG. 8.

Figure 8:
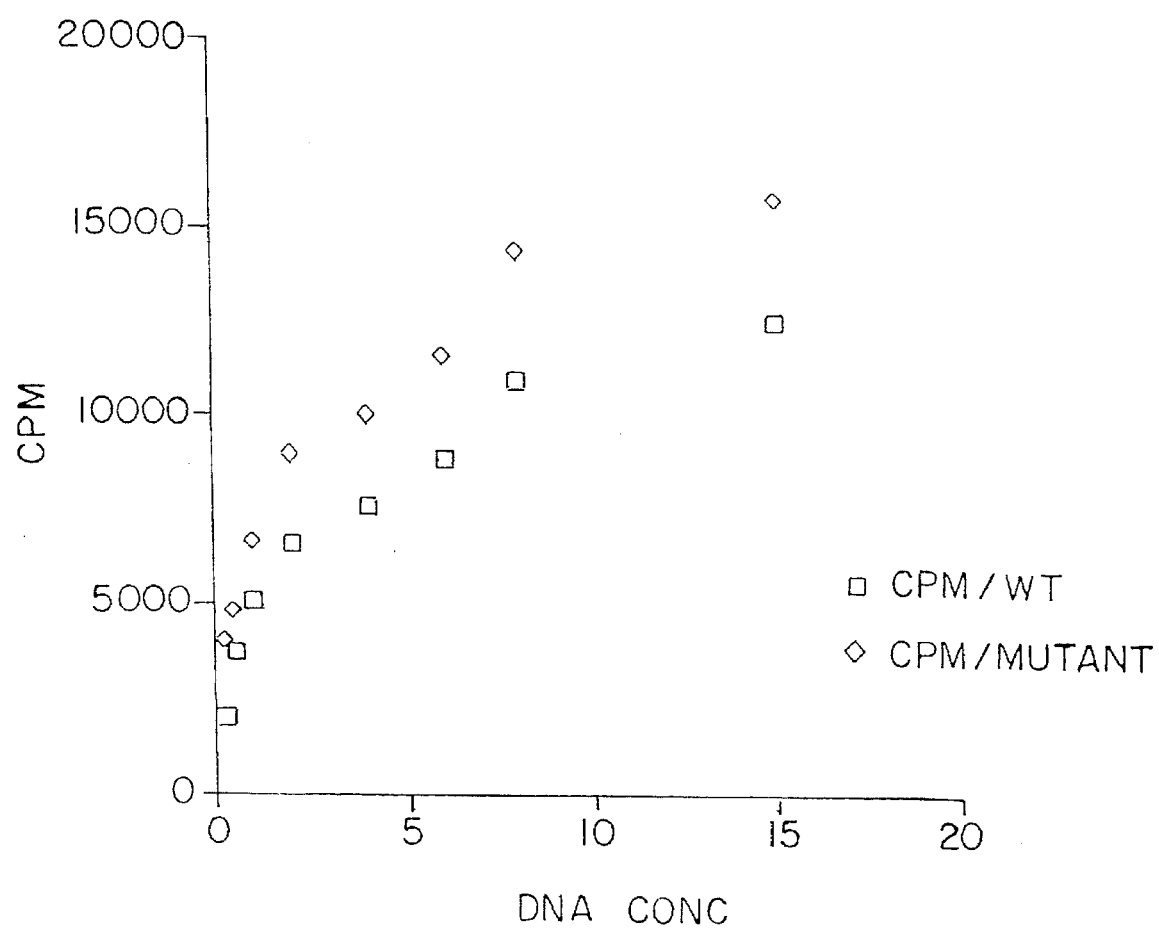
FIG. 8 shows the results of protein level assays performed using COS cells expressing wild-type and mutant progesterone receptor proteins.

As shown in FIG. 8, the mutant protein were present in cells at higher levels than the wild-type proteins. Each data point was tested in duplicate, and the results were found to be reproducible with different preparations of both the mutant and the wild-type receptor DNA. These results are consistent with that obtained in the Western blot assay.

While the invention has been described in detail, and with reference to specific embodiments thereof, it will be apparent to one of ordinary skill in the art that various changes and modifications can be made therein without departing from the spirit and scope thereof.

What is claimed:

1. A method for diagnosing an increased risk for breast or ovarian cancer comprising the steps of:

(A) obtaining, from a test subject, test nucleic acid comprising codon 660 within EXON 4 of the human progesterone receptor gene; and (B) assaying for the presence of a G to T point mutation in the first nucleotide of codon 660 within EXON 4 of the human progesterone receptor gene, wherein the presence of said point mutation in said test nucleic acid indicates an increased risk for breast or ovarian cancer.

2. The method of claim 1, wherein said method additionally comprises the steps of:

(C) obtaining, from said test subject, test nucleic acid which comprises codon 770 within EXON 5 of the human progesterone receptor gene, and (D) assaying for the presence of a C to T point mutation in the third nucleotide of codon 770 within EXON 5 of the human progesterone receptor gene, wherein the presence of said point mutation in said test nucleic acid comprising codon 770 of exons indicates an increased risk for breast or ovarian cancer.

3. The method of claims 1 or 2, wherein said method additionally comprises the steps of:
  (E) obtaining, from said test subject, test nucleic acid which comprises codon 897 within INTRON G of the human progesterone receptor gene, and
  (F) assaying for the presence of an Alu insertion within codon 897 within INTRON G of the human progesterone receptor gene,
wherein the presence of said Alu insertion in said test nucleic acid comprising codon 897 of INTRON G indicates an increased risk for breast or ovarian cancer.

4. The method of claim 1, wherein said assaying in step (B) is carried out by subjecting said test nucleic acid to BsrI restriction enzyme digestion, and assaying for the loss of a BsrI restriction site within EXON 4 of the human progesterone receptor gone, wherein the loss of said restriction site indicates the presence of said point mutation.

5. The method of claim 1, wherein said assaying in step (B) is carried out by sequencing said test nucleic acid.

6. The method of claim 1, wherein said assaying in step (B) is carried out by single-strand conformation polymorphism analysis.

7. The method of claim 1, wherein said assaying in step (B) is carried out by heteroduplex mapping.

8. The method of claim 2, wherein said assaying in step (D) is carried out by subjecting said test nucleic acid comprising codon 770 of EXON 5 to NlaIII restriction enzyme digestion, and assaying for the addition of a NlaIII restriction site within EXON 5 of the human progesterone receptor gene, wherein the addition of said restriction site indicates the presence of said point mutation.

9. The method of claim 2, wherein said assaying in step (D) is carried out by sequencing said test nucleic acid comprising codon 770 EXON 5.

10. The method of claim 2, wherein said assaying in step (D) is carried out by single-strand conformation polymorphism analysis.

11. The method of claim 2, wherein said assaying in step (D) is carried out by heteroduplex mapping.

12. The method of claim 3, wherein said assaying in step (F) is carried out by subjecting said test nucleic acid comprising codon 897 of INTRON G to TaqI restriction enzyme digestion, and assaying for the production of a 1.9 kb DNA fragment, wherein the production of said 1.9 kb DNA fragment indicates the presence of said Alu insertion.

13. The method of claim 3, wherein said assaying in step (F) is carried out by polymerase chain reaction using forward and reverse primers that border or are within INTRON G.

14. The method of claim 13, wherein said primers boarder INTRON G, and wherein said forward primer is:

5'-TTGATAACTTGCATGATGTAAGTA-3' (SEQ ID NO: 6),
and said reverse primer is:
5'-TGAAGTTGTTTGACAAGCTGTTGG-3' (SEQ ID NO: 7).

15. The method of claim 13, wherein said primers are within INTRON G, and wherein said forward primer is:

5'-GCCTCTAAAATGAAAGGCAGAAAGC-3' (SEQ ID NO: 8)
and said reverse primer is:
5'-CAAAAGTATTTTGTTGCTAAATGTCTG-3' (SEQ ID NO: 9).

16. The method of claim 3, wherein said assaying in step (F) is carried out by sequencing said test nucleic acid comprising codon 897 of INTRON G.

17. The method of claim 3, wherein said assaying in step (F) is carried out by heteroduplex mapping.

18. The method of claim 3, wherein said assaying in step (F) is carried out by florescent in situ hybridization using an oligonucleotide consisting of SEQ ID NO:10.

19. The method of claim 3, wherein said assaying in step (F) is carried out by Southern blotting using a probe comprising said Alu insertion.

20. The method of claim 1, wherein said test nucleic acid is obtained from cells within a body fluid of said subject, wherein said body fluid is selected from the group consisting of blood, ascites, pleural fluid and spinal fluid.

21. The method of claim 1, wherein said test nucleic acid is obtained from cells constituting a body tissue of said subject, wherein said body tissue is selected from the group consisting of skin, endometrial, uterine and cervical tissue.

22. The method of claim 1, wherein said test nucleic acid is genomic DNA, cDNA or mRNA.

23. The method of claim 2, wherein said test nucleic acid comprising codon 770 of EXON 5.

24. The method of claim 3, wherein said test nucleic acid used to assay for the Alu insertion in Step (F) is genomic DNA.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 3014 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

```
CTGACCAGCG CCGCCCTCCC CCGCCCCCGA CCCAGGAGGT GGAGATCCCT CCGGTCCAGC      60

CACATTCAAC ACCCACTTTC TCCTCCCTCT GCCCTATAT  TCCCGAAACC CCCTCCTCCT     120

TCCCTTTTCC CTCCTCCCTG GAGACGGGGG AGGAGAAAAG GGGAGTCCAG TCGTCATGAC     180

TGAGCTGAAG GCAAAGGGTC CCCGGGCTCC CCACGTGGCG GGCGGCCCGC CCTCCCCCGA     240

GGTCGGATCC CCACTGCTGT GTCGCCCAGC CGCAGGTCCG TTCCGGGGA  GCCAGACCTC     300

GGACACCTTG CCTGAAGTTT CGGCCATACC TATCTCCCTG GACGGGCTAC TCTTCCCTCG     360

GCCCTGCCAG GGACAGGACC CCTCCGACGA AAAGACGCAG GACCAGCAGT CGCTGTCGGA     420

CGTGGAGGGC GCATATTCCA GAGCTGAAGC TACAAGGGGT GCTGGAGGCA GCAGTTCTAG     480

TCCCCCAGAA AAGGACAGCG GACTGCTGGA CAGTGTCTTG GACACTCTGT GGCGCCCTC      540

AGGTCCCGGG CAGAGCCAAC CCAGCCCTCC CGCCTGCGAG GTCACCAGCT CTTGGTGCCT     600

GTTTGGCCCC GAACTTCCCG AAGATCCACC GGCTGCCCCC GCCACCCAGC GGGTGTTGTC     660

CCCGCTCATG AGCCGGTCCG GGTGCAAGGT TGGAGACAGC TCCGGGACGG CAGCTGCCCA     720

TAAAGTGCTG CCCCGGGGCC TGTCACCAGC CCGGCAGCTG CTGCTCCCGG CCTCTGAGAG     780

CCCTCACTGG TCCGGGCCC  CAGTGAAGCC GTCTCCGCAG GCCGCTGCGG TGGAGGTTGA     840

GGAGGAGGAT GGCTCTGAGT CCGAGGAGTC TGCGGGTCCG CTTCTGAAGG GCAAACCTCG     900

GGCTCTGGGT GGCGCGGCGG CTGGAGGAGG AGCCGCGGCT GTCCGCCGG  GGGCGGCAGC     960

AGGAGGCGTC GCCCTGGTCC CCAAGGAAGA TTCCCGCTTC TCAGCGCCCA GGGTCGCCCT    1020

GGTGGAGCAG GACGCGCCGA TGGCGCCCGG GCGCTCCCCG CTGGCCACCA CGGTGATGGA    1080

TTTCATCCAC GTGCCTATCC TGCCTCTCAA TCACGCCTTA TTGGCAGCCC GCACTCGGCA    1140

GCTGCTGGAA GACGAAAGTT ACGACGGCGG GGCCGGGGCT GCCAGCGCCT TGCCCCGCC     1200

GCGGAGTTCA CCCTGTGCCT CGTCCACCCC GGTCGCTGTA GGCGACTTCC CCGACTGCGC    1260

GTACCCGCCC GACGCCGAGC CCAAGGACGA CGCGTACCCT CTCTATAGCG ACTTCCAGCC    1320

GCCCGCTCTA AAGATAAAGG AGGAGGAGGA AGGCGCGGAG GCCTCCGCGC GCTCCCCGCG    1380
```

-continued

```
TTCCTACCTT GTGGCCGGTG CCAACCCCGC AGCCTTCCCG GATTTCCCGT TGGGGCCACC    1440
GCCCCCGCTG CCGCCGCGAG CGACCCCATC CAGACCCGGG GAAGCGGCGG TGACGGCCGC    1500
ACCCGCCAGT GCCTCAGTCT CGTCTGCGTC CTCCTCGGGG TCGACCCTGG AGTGCATCCT    1560
GTACAAAGCG GAGGGCGCGC CGCCCCAGCA GGGCCCGTTC GCGCCGCCGC CCTGCAAGGC    1620
GCCGGGCGCG AGCGGCTGCC TGCTCCCGCG GGACGGCCTG CCCTCCACCT CCGCCTCTGC    1680
CGCCGCCGCC GGGCGGCCC CCGCGCTCTA CCCTGCACTC GGCCTCAACG GCTCCCGCA     1740
GCTCGGCTAC CAGGCCGCCG TGCTCAAGGA GGGCCTGCCG CAGGTCTACC CGCCCTATCT    1800
CAACTACCTG AGGCCGGATT CAGAAGCCAG CCAGAGCCCA CAATACAGCT TCGAGTCATT    1860
ACCTCAGAAG ATTTGTTTAA TCTGTGGGGA TGAAGCATCA GGCTGTCATT ATGGTGTCCT    1920
TACCTGTGGG AGCTGTAAGG TCTTCTTTAA GAGGGCAATG GAAGGGCAGC ACAACTACTT    1980
ATGTGCTGGA AGAAATGACT GCATCGTTGA TAAAATCCGC AGAAAAACT GCCCAGCATG     2040
TCGCCTTAGA AAGTGCTGTC AGGCTGGCAT GGTCCTTGGA GGTCGAAAAT TTAAAAAGTT    2100
CAATAAAGTC AGAGTTGTGA GAGCACTGGA TGCTGTTGCT CTCCCACAGC CAGTGGGCGT    2160
TCCAAATGAA AGCCAAGCCC TAAGCCAGAG ATTCACTTTT TCACCAGGTC AAGACATACA    2220
GTTGATTCCA CCACTGATCA ACCTGTTAAT GAGCATTGAA CCAGATGTGA TCTATGCAGG    2280
ACATGACAAC ACAAAACCTG ACACCTCCAG TTCTTTGCTG ACAAGTCTTA ATCAACTAGG    2340
CGAGAGGCAA CTTCTTTCAG TAGTCAAGTG GTCTAAATCA TTGCCAGGTT TTCGAAACTT    2400
ACATATTGAT GACCAGATAA CTCTCATTCA GTATTCTTGG ATGAGCTTAA TGGTGTTTGG    2460
TCTAGGATGG AGATCCTACA AACACGTCAG TGGGCAGATG CTGTATTTTG CACCTGATCT    2520
AATACTAAAT GAACAGCGGA TGAAAGAATC ATCATTCTAT TCATTATGCC TTACCATGTG    2580
GCAGATCCCA CAGGAGTTTG TCAAGCTTCA AGTTAGCCAA GAAGAGTTCC TCTGTATGAA    2640
AGTATTGTTA CTTCTTAATA CAATTCCTTT GGAAGGGCTA CGAAGTCAAA CCCAGTTTGA    2700
GGAGATGAGG TCAAGCTACA TTAGAGAGCT CATCAAGGCA ATTGGTTTGA GGCAAAAAGG    2760
AGTTGTGTCG AGCTCACAGC GTTTCTATCA ACTTACAAAA CTTCTTGATA ACTTGCATGA    2820
TCTTGTCAAA CAACTTCATC TGTACTGCTT GAATACATTT ATCCAGTCCC GGGCACTGAG    2880
TGTTGAATTT CCAGAAATGA TGTCTGAAGT TATTGCTGCA CAATTACCCA AGATATTGGC    2940
AGGGATGGTG AAACCCCTTC TCTTTCATAA AAAGTGAATG TCATCTTTTT CTTTTAAAGA    3000
ATTAAATTTT GTGG                                                     3014
```

( 2 ) INFORMATION FOR SEQ ID NO:2:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:2:

```
GTCGAAAATT TAAAAAGTTC AATAAAGTCA GAGTTGTGAG AGCACTGGAT GCTGTTGCTC      60
TCCCACAGCC AGTGGGCGTT CCAAATGAAA GCCAAGCCCT AAGCCAGAGA TTCACTTTTT    120
CACCAGGTCA AGACATACAG TTGATTCCAC CACTGATCAA CCTGTTAATG AGCATTGAAC    180
CAGATGTGAT CTATGCAGGA CATGACAACA CAAAACCTGA CACCTCCAGT TCTTTGCTGA    240
```

```
CAAGTCTTAA TCAACTAGGC GAGAGGCAAC TTCTTTCAGT AGTCAAGTGG TCTAAATCAT    300

TGCCAG                                                              306
```

( 2 ) INFORMATION FOR SEQ ID NO:3:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:3:

```
GTTTTCGAAA CTTACATATT GATGACCAGA TAACTCTCAT TCAGTATTCT TGGATGAGCT     60

TAATGGTGTT TGGTCTAGGA TGGAGATCCT ACAAACACGT CAGTGGGCAG ATGCTGTATT    120

TTGCACCTGA TCTAATACTA AATGA                                         145
```

( 2 ) INFORMATION FOR SEQ ID NO:4:

( i ) SEQUENCE CHARACTERISTICS:
        ( A ) LENGTH: 149 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:4:

```
AAAATAAAAA GAAACTTGAA GGAAATAAAC ACCAGTGCAG AGAACGAAAG AAAACTTCTA     60

ACATCCTCAG AGAAATAAGA ATGATACGGT ATCCATGACA TGAGAACAGA AAACATTTTT    120

AAAACAGACA TTAGCAAGA AAATACGCG                                      149
```

( 2 ) INFORMATION FOR SEQ ID NO:5:

( i ) SEQUENCE CHARACTERISTICS:
        ( A ) LENGTH: 320 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:5:

```
TTTTTTTTT TTTTTTTTT TTTTGAGAC GGAGTCTGGC TCTGTCGCCC AGGCTGGAGT       60

GCAGTGGCGG GATCTCGGCT CACTGCAAGC TCCGCCTCCC GGGTTCACGC CATTCTCCTG   120

CCTCAGCCTC CCAAGTAGCT GGGACTACAG GCGCCCGCCA CTACGCCCAG CTAATTTTTT   180

GTATTTTTAG TAGAGACGGG GTTTCACCGT TTTAGCCAGG ATGGTCTCGA TCTCCTGACC   240

TCGTGATCCG CCCGCCTCGG CCTCCCAAAG TGCTGGGATT ACAGGCGTGA GCCACCGCGC   300

CCGGCCCAGA AAACATTTTT                                               320
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single ( D ) TOPOLOGY: linear ( i i ) MOLECULE TYPE: DNA ( i i i ) HYPOTHETICAL: NO ( x i ) SEQUENCE DESCRIPTION: SEQ ID NO:6:

TTGATAACTT GCATGATGTA AGTA 24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:7:

TGAAGTTGTT TGACAAGCTG TTGG 24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:8:

GCCTCTAAAA TGAAAGGCAG AAAGC 25

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:9:

CAAAAGTATT TTGTTGCTAA ATGTCTG 27

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:10:

AAAGTGCTGG GATTACAGG 19

( 2 ) INFORMATION FOR SEQ ID NO:11:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( x i ) SEQUENCE DESCRIPTION: SEQ ID NO:11:

GGAATTCGTC GAAAATTTAA AAAGTTCA                    28

( 2 ) INFORMATION FOR SEQ ID NO:12:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( x i ) SEQUENCE DESCRIPTION: SEQ ID NO:12:

GGAATTCCTG GCAATGATTT AGACCACT                    28

( 2 ) INFORMATION FOR SEQ ID NO:13:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( x i ) SEQUENCE DESCRIPTION: SEQ ID NO:13:

GGAATTCGTT TTCGAAACTT ACATATTG                    28

( 2 ) INFORMATION FOR SEQ ID NO:14:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( x i ) SEQUENCE DESCRIPTION: SEQ ID NO:14:

GGAATTCTCA TTTAGTATTA GATCAGGT                    28